United States Patent
Ranade

(10) Patent No.: US 8,052,989 B2
(45) Date of Patent: Nov. 8, 2011

(54) METHOD OF INCORPORATING CARBON NANOTUBES IN A MEDICAL APPLIANCE, A CARBON NANOTUBE MEDICAL APPLIANCE, AND A MEDICAL APPLIANCE COATED USING CARBON NANOTUBE TECHNOLOGY

(75) Inventor: Shrirang V. Ranade, Arlington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 12/644,939

(22) Filed: Dec. 22, 2009

(65) Prior Publication Data

US 2010/0098741 A1    Apr. 22, 2010

Related U.S. Application Data

(62) Division of application No. 10/980,914, filed on Nov. 3, 2004, now abandoned.

(51) Int. Cl.
*A61K 6/083* (2006.01)
*A61F 2/00* (2006.01)
*A61F 2/82* (2006.01)
*B05D 3/00* (2006.01)

(52) U.S. Cl. ....... 424/423; 623/1.15; 977/742; 977/746; 977/752

(58) Field of Classification Search .................. None
See application file for complete search history.

(56) References Cited

U.S. PATENT DOCUMENTS

| | | | |
|---|---|---|---|
| 5,824,049 A | 10/1998 | Ragheb et al. | |
| 6,096,070 A | 8/2000 | Ragheb et al. | |
| 6,368,569 B1 | 4/2002 | Haddon et al. | |
| 6,875,374 B1 | 4/2005 | Zhan et al. | |
| 7,364,585 B2 | 4/2008 | Weber | |
| 7,473,411 B2* | 1/2009 | Ajayan et al. | 423/447.1 |
| 7,491,753 B2 | 2/2009 | Krishnan | |
| 2002/0001620 A1 | 1/2002 | Pienkowski et al. | |
| 2002/0049495 A1 | 4/2002 | Kutryk | |
| 2003/0065355 A1 | 4/2003 | Weber | |
| 2003/0153965 A1 | 8/2003 | Supronowicz et al. | |

FOREIGN PATENT DOCUMENTS

| | | |
|---|---|---|
| WO | 03092763 A | 11/2003 |
| WO | 2004011703 A | 2/2004 |

OTHER PUBLICATIONS

Chakrapani, Nirupama, et al., "Capillarity-driven assembly of two-dimensional cellular carbon nanotube foams," Proceedings of the National Academy of Sciences, Mar. 23, 2004, pp. 4009-4012, vol. 101, No. 12.

Thostenson, Erik T., et al., "Advances in the science and technology of carbon nanotubes and their composites: a review," Composites Science and Technology 61, 2001, pp. 1899-1912.

Harutyunyan, A. R., et al., "Carbon Nanotubes for Medical Applications," European Cells and Materials, 2002, pp. 84-87, vol. 3, Suppl. 2.

* cited by examiner

*Primary Examiner* — Shanon A Foley

(74) *Attorney, Agent, or Firm* — Kenyon & Kenyon LLP

(57) ABSTRACT

A method of coating a medical device, such as a stent or balloon. The method comprises assembling an array of vertically-oriented carbon nanotubes on a surface of the medical device and contacting the array of carbon nanotubes with a liquid. The liquid is evaporated to form a cellular foam made of carbon nanotubes. The liquid may contain a bioactive agent. Also described are medical devices having a coating of cellular foam that is made of carbon nanotubes.

13 Claims, 7 Drawing Sheets

METHOD OF INCORPORATING CARBON NANOTUBES IN A MEDICAL APPLIANCE, A CARBON NANOTUBE MEDICAL APPLIANCE, AND A MEDICAL APPLIANCE COATED USING CARBON NANOTUBE TECHNOLOGY

CROSS-REFERENCE TO RELATED APPLICATIONS

This application is a divisional of Application Ser. No. 10/980,914 filed Nov. 3, 2004, of which this application claims the benefit.

FIELD OF THE INVENTION

The present invention relates to coating methods. More particularly, the present invention relates to a method for improving the quality of a coating and performance of a drug coated device such as a stent by utilizing carbon nanotubes in the coating.

BACKGROUND INFORMATION

Medical devices may be coated so that the surfaces of such devices have desired properties or effects. For example, it may be useful to coat medical devices to provide for the localized delivery of therapeutic agents to target locations within the body, such as to treat localized disease (e.g., heart disease) or occluded body lumens. Localized drug delivery may avoid some of the problems of systemic drug administration, which may be accompanied by unwanted effects on parts of the body which are not to be treated. Additionally, treatment of the afflicted part of the body may require a high concentration of therapeutic agent that may not be achievable by systemic administration. Localized drug delivery may be achieved, for example, by coating balloon catheters, stents and the like with the therapeutic agent to be locally delivered. The coating on medical devices may provide for controlled release, which may include long-term or sustained release, of a bioactive material.

Aside from facilitating localized drug delivery, medical devices may be coated with materials to provide beneficial surface properties. For example, medical devices are often coated with radiopaque materials to allow, for fluoroscopic visualization while placed in the body. It is also useful to coat certain devices to achieve enhanced biocompatibility and to improve surface properties such as lubriciousness.

Coatings have been applied to medical devices by processes such as dipping, spraying, vapor deposition, plasma polymerization, spin-coating and electrodeposition.

The spray-coating method has been used because of its excellent features, e.g., good efficiency and control over the amount or thickness of coating. In the spin-dipping process, a medical device is coupled to a spinning device, and then, while rotating about a central axis, the medical device is dipped into a coating solution to achieve the desired coating.

In addition to the spray coating and spin-dipping methods, the electrostatic deposition method has been suggested for coating medical devices. For example, U.S. Pat. Nos. 5,824,049 and 6,096,070 to Ragheb et al. mention the use of electrostatic deposition to coat a medical device with a bioactive material. In the conventional electrodeposition or electrostatic spraying method, a surface of the medical device is electrically grounded and a gas may be used to atomize the coating solution into droplets. The droplets are then electrically charged using, for example, corona discharge, i.e., the atomized droplets are electrically charged by passing through a corona field. Since the droplets are charged, when they are applied to the surface of the medical device, they will be attracted to the surface since it is grounded.

Another method of coating a device can be achieved with electrohydrodynamic spraying. Using this method, a gas is not needed to disperse the coating. Electrohydrodynamic coating is accomplished by forcing a compatible solution through a nozzle assembly that has been electrically charged. The coating solution passes through the charged nozzle where it is electrically charged. As the solution exits the nozzle, the solution atomizes as the charged particles repel each other. This action forms the spray mist. The charged particles are attracted to the device to be coated since the device is connected to an electrical ground.

Devices may be coated by a gas assisted spraying process. A polymer/drug combination may be dissolved in a solvent mixture. The solution may be sprayed onto the devices and a polymer/drug film may be formed when the solvents evaporate. The ability to apply thin coatings on products may be limited by the capabilities of a gas assisted spraying process. The coating may flow on the medical device prior to drying, thereby creating an uneven concentration of bioactive agent on the surface of the device. A gas assisted spraying process may have a high variability for thin coatings.

Conventional methods of coating stents or devices with a drug-polymer layer, such as spraying or dipping, may require a solution of the drug-polymer to physically wet the surface of the stent. Spraying or dipping may cause uneven and unpredictable wetting, and distribution and evaporation of the solvent molecules may result in a non-uniform coating. The drying of the coating may lead to cracking and/or points of stress in the coating. A non-uniform coating may lead to the unit failing agent release requirements, drug uniformity and coating thickness specifications.

Conventional drug-eluting stents may include paclitaxel particles incorporated into a polymer matrix. The polymer may be hydrophobic and may entrap a large amount of drug (for instance, possibly over 95% in the 8.8% formulation of Boston Scientific's TAXUS SR drug eluting stent) that may not be subsequently delivered when implanted in a lumen of a human body. There may be government regulatory issues regarding sequestered drug that may remain entrapped indefinitely, as well as safety concerns.

There is, therefore, a need for a cost-effective method of coating devices that results in uniform, defect-free coatings and uniform drug doses per unit device. The method would provide better control of the agent release profile of the device, including releasing a higher percentage of the bioactive agent. The method would also improve the quality of the coating of the device by removing defects, cracks and stress points in the coating. Each of the references cited herein is incorporated by reference herein for background information.

SUMMARY

A method of coating an article is provided. The method includes: preparing a solution including a bioactive agent and a carbon nanotube precursor; treating the solution to form carbon nanotubes; and applying the solution to the article.

The treating of the solution may include waiting a predetermined period of time, drying the solution, heating the solution, and/or exposing the solution to one of a vacuum and a partial vacuum. The applying of the solution may include dip-coating and/or spray-coating. The carbon nanotubes may have have a diameter of between about 1 nanometer and about 100 nanometers.

After the treating operation, the solution may have a density of carbon nanotubes sufficient to create a multiple walled carbon nanotube array. After the treating operation, the solution may have a density of carbon nanotubes sufficient to create a porosity in a polymer matrix. After the treating operation, the solution may have a density of carbon nanotubes sufficient to create a nanotube foam operating as a membrane.

The carbon nanotubes may be self-assembling. The solution may include a polymer. The polymer may include polystyrene, polyisobutylene, butyl acrylate, and/or polyvinyl alcohol. The solution may include tetrahydrofurane. A composition of the carbon nanotube precursor may determine a diameter of at least some of the carbon nanotubes. The solution may further include a further carbon nanotube precursor. Another composition of the further carbon nanotube precursor may determine another diameter of at least some others of the carbon nanotubes.

The article, when implanted in a lumen of a human body, may release the bioactive agent via the carbon nanotubes.

A method of producing a medical device is provided. The method includes: forming a core of the medical device with a pattern on a surface of the core and assembling a multi-walled carbon nanotube array on the pattern on the surface. The pattern on the surface may determine an orientation of the multi-walled carbon nanotube array.

The method may include contacting a first part of the multi-walled carbon nanotube array with a first bioactive agent dissolved in a first solution. The orientation of the multi-walled nanotube array may determine a release rate of the first bioactive agent. The method may include contacting a second part of the multi-walled carbon nanotube array with a second bioactive agent dissolved in a second solution.

A method of manufacturing a medical appliance is provided. The method includes creating a mixture of a carbon nanotube precursor and a polymer and injecting the mixture into a mold. The mold forms the mixture into a shape of the medical appliance.

The method may include treating the mixture to form a plurality of carbon nanotubes. The treating operation may be performed before and/or after the injecting operation.

The method may further include contacting the medical appliance with a coating including a bioactive agent.

A method of forming a nanotube tissue scaffold is provided. The method includes forming a nanotube precursor and treating the nanotube precursor to form the nanotube tissue scaffold. The nanotube tissue scaffold is electrically conductive.

The method may include implanting the nanotube tissue scaffold in a lumen of a human body.

DETAILED DESCRIPTION

Figure 1:
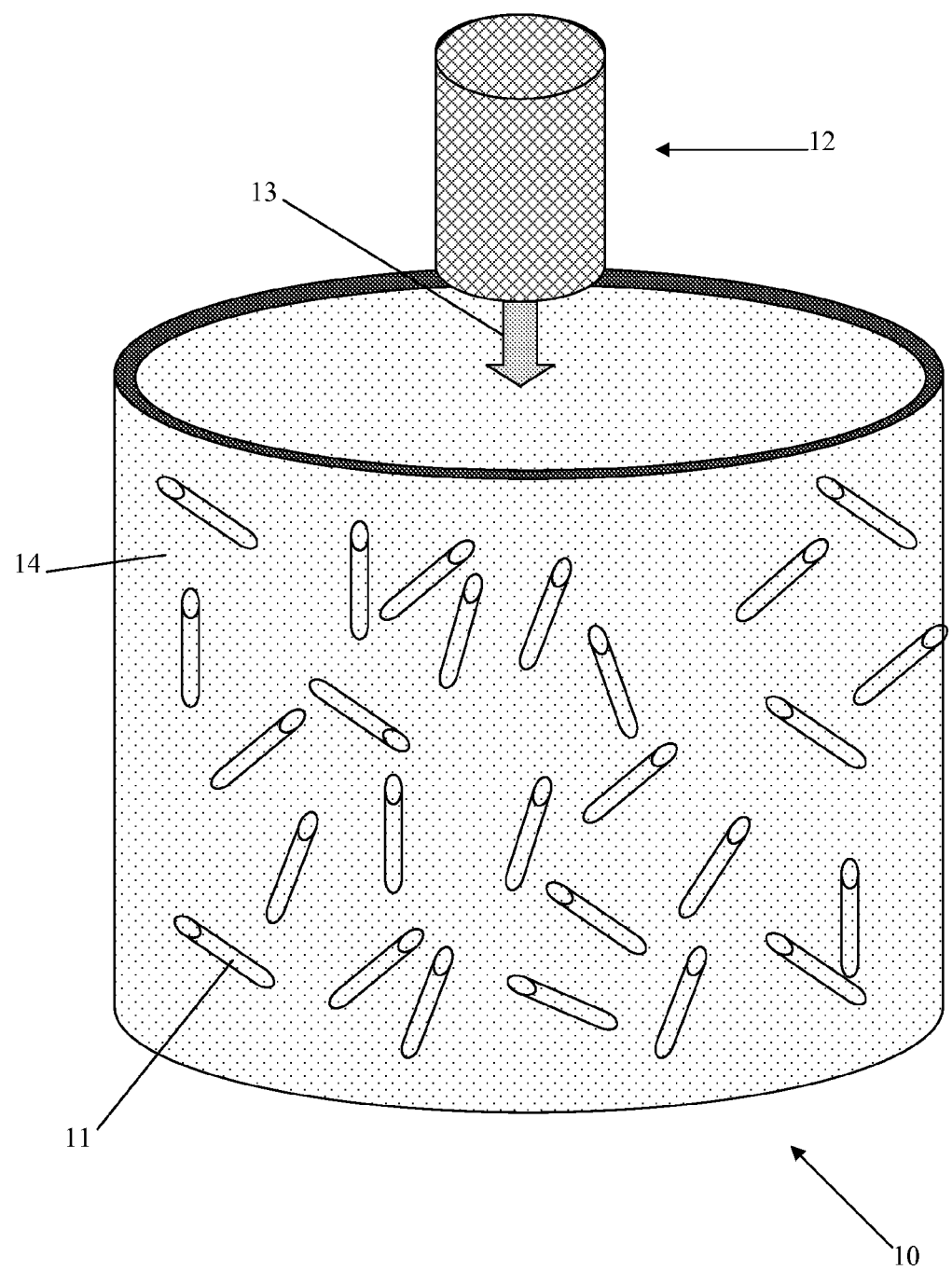
FIG. 1 shows a stent being dipcoated in a mixture including nanotubes.

A nanoporous or mesoporous drug delivery coating or tissue engineering scaffold may be formed by the use of self-assembled cellular carbon nanotube foams (as a coating by itself) or may be blended in with another drug delivery carrier such as a polymer. The polymer may include polystrene, polyisobutylene copolymers, and/or styrene-isobutylene-styrene block copolymers such as styrene-isobutylene-styrene tert-block copolymers (SIBS). The incorporation of carbon nanotubes into the polymer may generate a nanoporous structure within the polymer drug delivery carrier.

Multi-walled carbon nanotube (MWNT) arrays may be assembled into contiguous cellular foams via the use of capillary forces that arise during the evaporation of liquids. For example, see the article "Capillarity-driven assembly of two-dimensional cellular nanotube foams" by Chakrapani et al, PNAS, Mar. 23, 2004, pages 4009-4012.

Nanotube foams may be formed in-situ in a coating formulation via the self-assembly of the nanotubes as the processing solvents are dried. The pattern formation with the nanotubes may be dependent on the use of solvents for processing and the self-assembly may only occur during the drying step. The formation of the foam may facilitate the formation of a coating or film that may be used in controlled release of therapeutics or as a tissue-engineering scaffold. The foam may lead to the formation of an interconnected network providing pathways for drug delivery applications.

Alternately, the possibility of making blends of nanotubes with polymeric carriers by mixing in with solvents such as tetrahydrofurane (THF). The blends may be formed with drug delivery polymers that may be advantageous from a biocompatibility perspective (such as SIBS, butyl acrylate, polyvinyl alcohol, etc.).

The incorporation of nanotubes may lead to the in-situ formation of pores (also referred to herein as voids) in a coating used for drug delivery. This may enable the subsequent filling of these pores or voids with drugs, therapeutics or biologically active agents so that the interconnected pathways formed by the presence of these nanotubes facilitate controlled delivery of therapeutics.

The incorporation of nanotubes may lead to the in-situ formation of pores or voids in a monolithic device that is composed of a pure or nearly pure nanotubes, or nanotubes in a polymer (or other appropriate material) matrix.

The therapeutics may be loaded in the coating as part of the solvent-processing step, for instance prior to spray coating, or may be loaded into the coating by a subsequent process (for example, spraying or dip-coating).

The use of a patterned substrate to assemble the MWNT foam may facilitate the formation of a drug delivery device. The orientation of the MWNT foam may be controlled via the pattern on the substrate. This may enable accurate determination of therapeutic delivery rates on a device. Additionally, by providing different patterns on different portions of the substrate, it may be possible to tune different release rates for multiple drugs in different locations on the same device.

The formation of a porous matrix by embedding nanotubes in a polymer matrix may be advantageous in enabling bioactive agents that are sequestered in the matrix to be migrate out of the matrix, as non-porous polymers may tend to trap the bioactive agent. An exemplary embodiment of the present invention may allow the release of a large percentage, or even the entire amount, of drug that is in the matrix.

A polymer matrix with a tunable porosity may be advantageous in tissue engineering. The porosity of a polymer matrix may be tunable by increasing or decreasing the concentration of nanotubes in the matrix, or by changing the size (diameter and/or length) of the nanotubes.

In an alternative exemplary embodiment, the therapeutic may be dispersed in the coating solution rather than be soluble in the coating solvents.

In an alternative exemplary embodiment, the MWNT containing coating may be applied in layers consisting of drug containing layers of varying drug concentrations and non-drug containing layers used as controlled release porous barriers over drug containing layers.

In an alternative exemplary embodiment, the MWNT containing coating may be used as membrane to modulate drug release.

In an alternative exemplary embodiment, macroscopic MWNT may be used as a coating itself. In an alternative exemplary embodiment, MWNT may be incorporated as an additive in drug delivery coatings to modulate release.

In an alternative exemplary embodiment, carbon nanotubes may operate as a tissue engineering scaffold.

FIG. 1 shows stent 12 being dipcoated the direction of arrow 13 into mixing container 10. Mixing container 10 includes nanotubes 11 and bioactive agent 14. Mixing container 10 may also include a polymer (for instance SIBS) and a solvent. A precursor material for nanotubes 11 may be introduced into mixing container 10 and then treated in order to promote the development of nanotubes 11. The treatment process may include heating, pressure, and/or waiting a predetermined period of time. The parameters of the treatment process may be adjusted in order to change the characteristics of the resulting nanotubes 11. Additionally, the precursor material may be selected in order to change the characteristics of the resulting nanotubes 11, including diameter and/or length.

Figure 2:
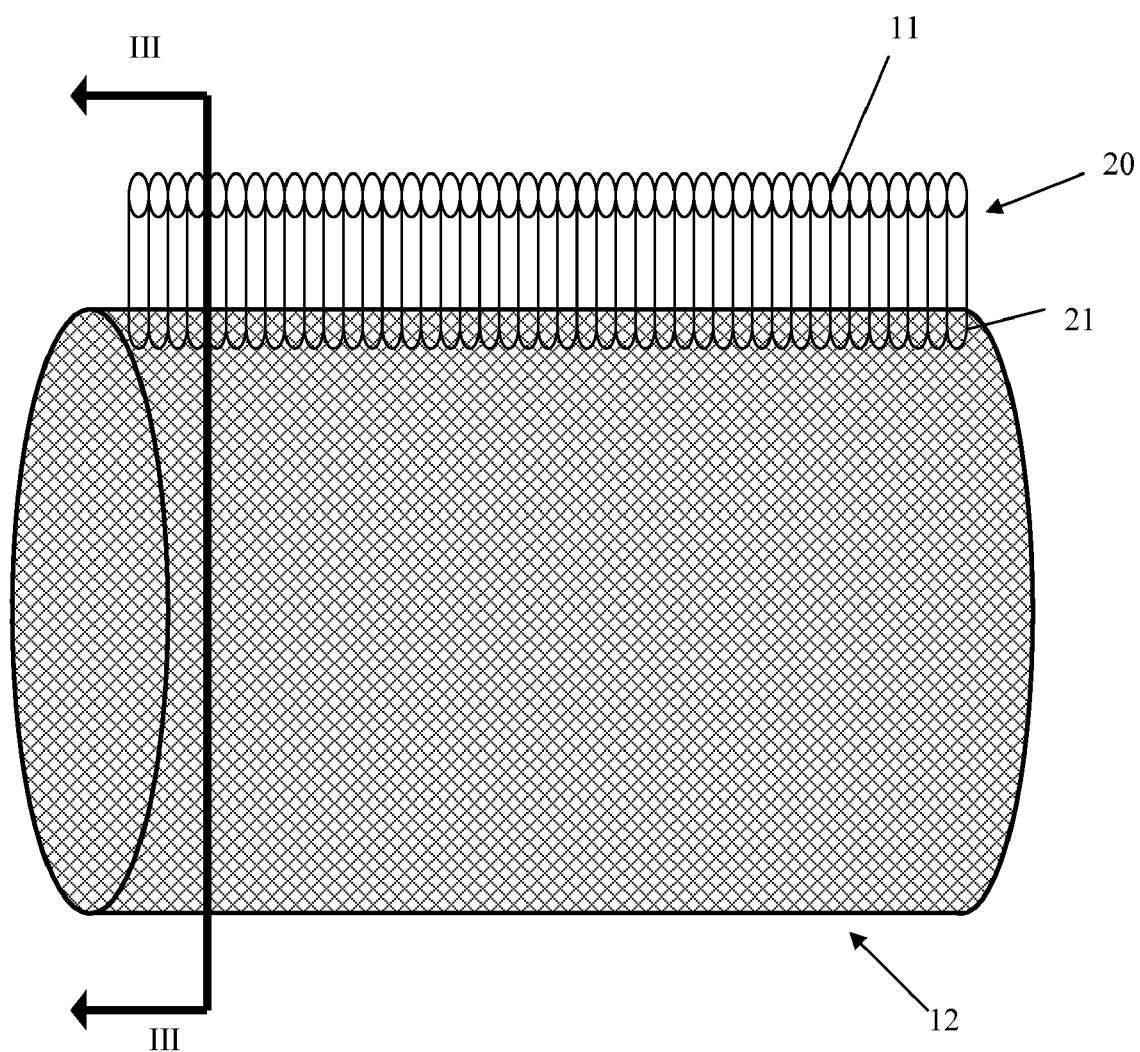
FIG. 2 shows a stent with a portion of a multi-walled nanotube array shown.

FIG. 2 shows stent 12 with multi-walled nanotube array (MWNT) row 20. MWNT row 20 is composed of nanotubes 11. Nanotubes 11 may attach to stent 12 in a uniform vertical orientation to form MWNT row 20. Other rows of MWNT may be arranged on stent 12, and are not shown for the sake of clarity. MWNT row 20 may grow on stent 12 while stent 12 is submerged (for example, dipped) in a solution including a precursor material for nanotubes 11. MWNT row 20 may grow to a specified length based on the time that stent 12 is submerged in the solution of nanotube precursor material. The nanotube precursor material may determine the diameter of nanotubes 11. Stent 12 may have pattern 21 on an external surface to encourage the growth of MWNT row 20. Different patterns may also be present on stent 12 to promote the growth of different nanotubes, for example from different nanotube precursor materials.

Figure 3:
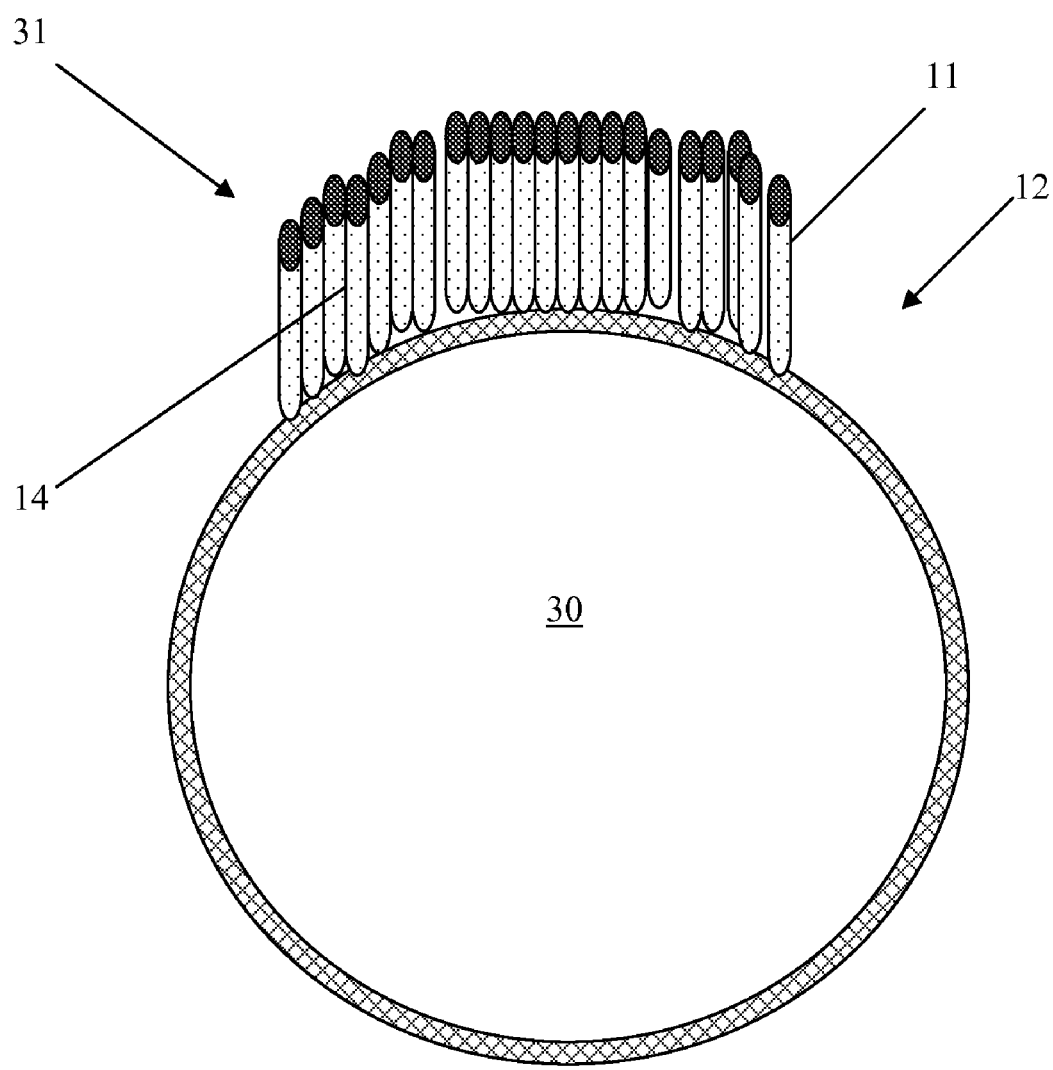
FIG. 3 shows the stent of FIG. 2 cut along line III-III and showing a multi-walled nanotube array.

FIG. 3 shows stent 12 of FIG. 2 cut along line and showing a portion of multi-walled nanotube array, namely MWNT section 31. Stent 12 is shown with interior space 30, which in the case of stent 12 is the space through which flow of, for instance, air or blood occurs after implanting stent 12 in a human body. Nanotubes 11 of MWNT section 31 contain bioactive agent 14. Bioactive agent 14 may be introduced into nanotubes 11 prior to attachment of nanotubes 11 to stent 12 in MWNT section 30. Alternatively, nanotubes 11 may form MWNT section 30 on stent 12 with another solution, air, or another gas in the interior spaces of nanotubes 11. Bioactive agent 14 may then be introduced into nanotubes 11 by spraying or dipcoating stent 12 having MWNT section 31 with a solution including bioactive agent 14.

Figure 4:
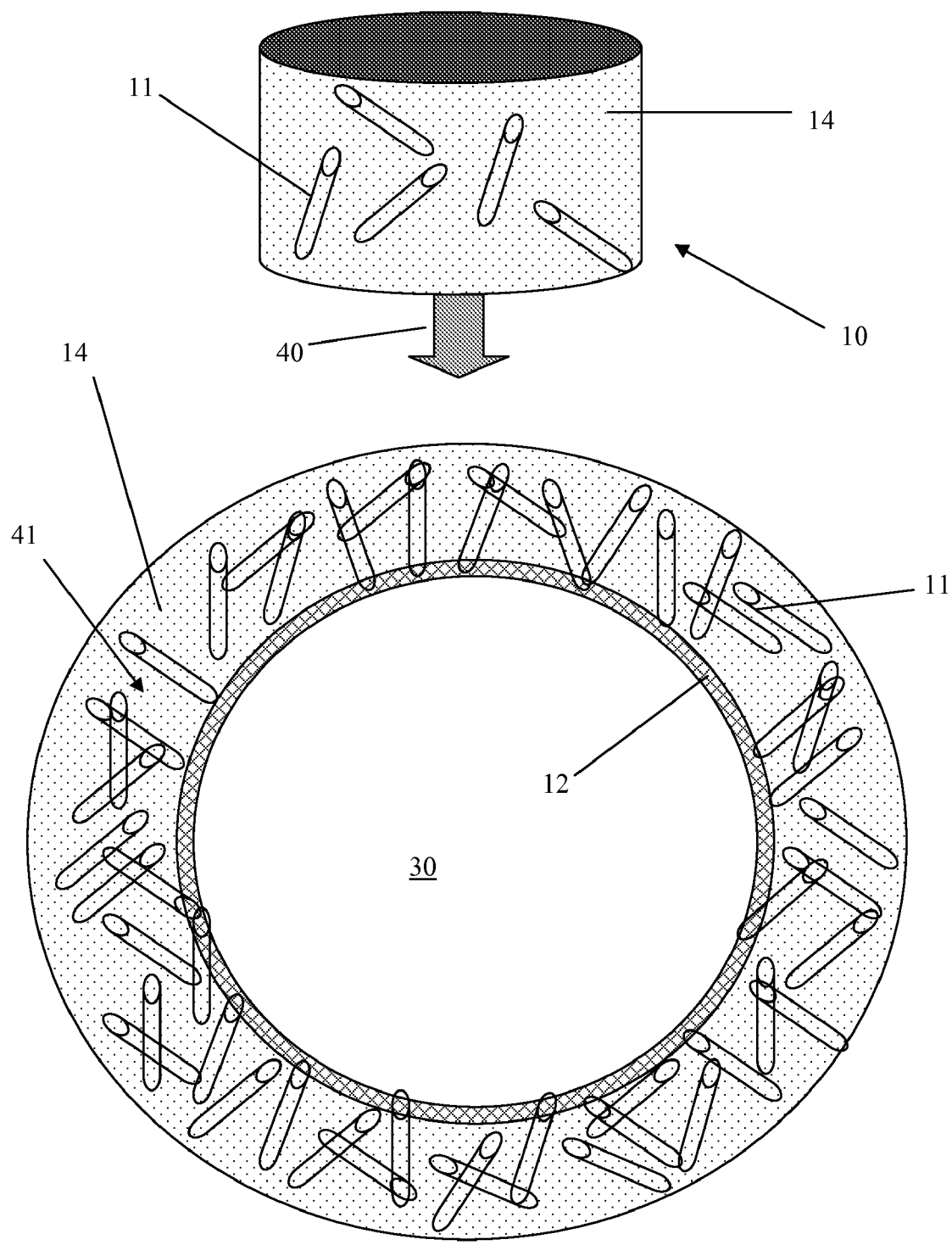
FIG. 4 shows a stent being sprayed with a polymer coating including nanotubes.

FIG. 4 shows stent 12 being sprayed with a solution including nanotubes 11 from mixing container 10. Mixing container 10 includes nanotubes 11 and bioactive agent 14. Mixing container 10 is coupled to spray nozzle 40, which may be a high-pressure nozzle, an ultrasonic nozzle, and/or a nozzle imparting an electrostatic charge to material being sprayed. Stent 12 is shown from the same perspective as shown in FIG. 3, namely a cross-sectional view. Stent 12 defines interior space 30. On an exterior of stent 12, polymer matrix 41 may include bioactive agent 14 and nanotubes 11. Nanotubes 11 may provide increased porosity to polymer matrix 41, and may therefore promote the release of bioactive agent 14 subsequent to implant of stent 12 in a human body. Polymer matrix 41 may also be coated on the inside of stent 12, and/or on any exposed portion of stent 12. Polymer matrix 41 may include a polymer, which may be included in mixing container 10 and may be sprayed simultaneously with bioactive agent 14 and nanotubes 11 onto stent 12. Additionally, a solvent may be included in the mixture sprayed onto stent 12. Evaporation of the solvent from the mixture subsequent to spraying may promote the creation of polymer matrix 41.

Figure 5:
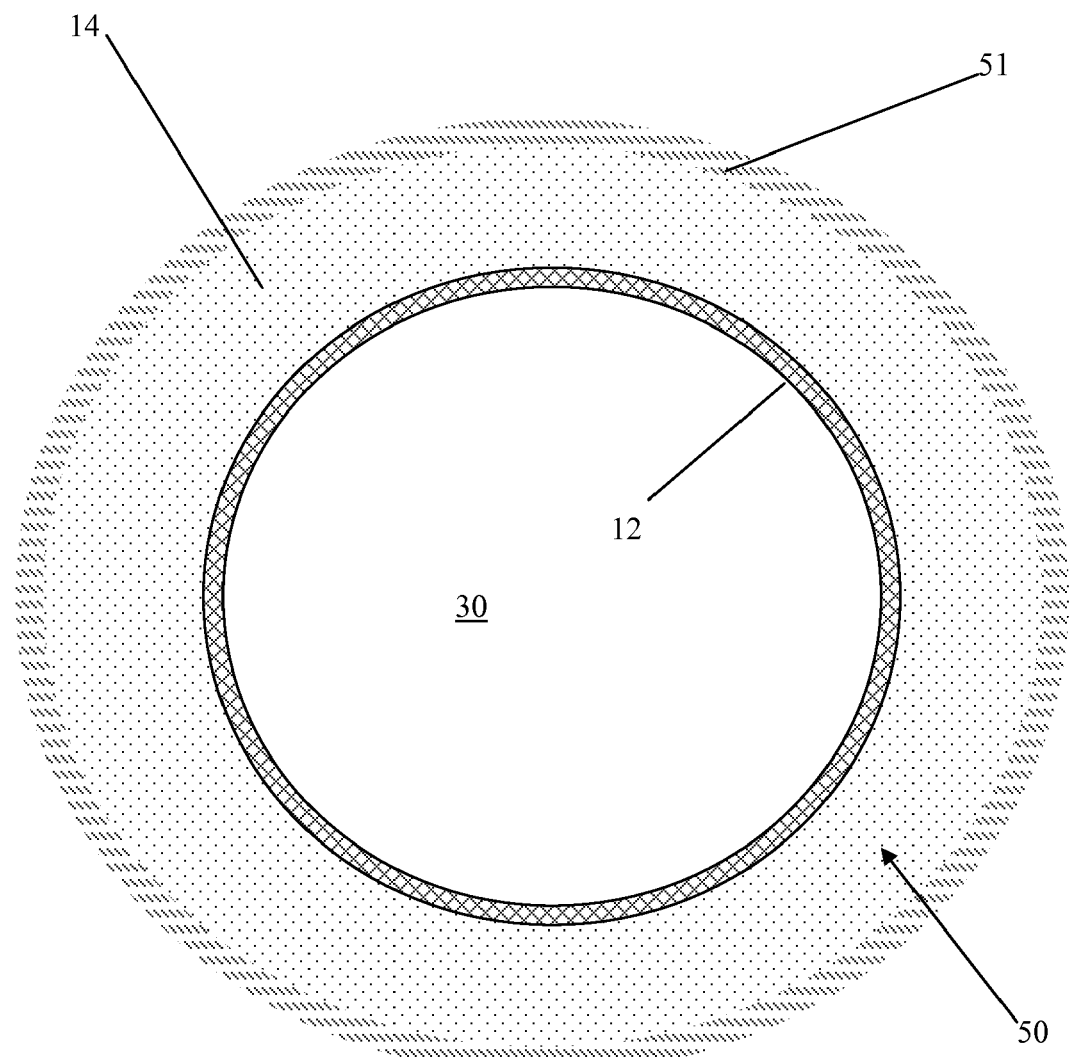
FIG. 5 shows a stent with a polymer coating having an outer membrane including nanotubes.

FIG. 5 shows stent 12 with polymer coating 50 having outer nanotube membrane 51 including nanotubes. Stent 12 is shown from the same perspective as shown in FIG. 3, namely a cross-sectional view. Stent 12 defines interior space 30. On an exterior of stent 12, polymer coating 50 may include bioactive agent 14. Additionally, polymer coating 50 may include a polymer, a solvent, nanotubes, and/or any other appropriate material. Nanotubes in solution may be spray coated and/or dip-coated on stent 12 including polymer coating 50. The solvent may be evaporated from the solution by heating, vacuum and/or by waiting a predetermined period. The nanotubes may be allowed to form a multi-walled nanotube array prior to evaporating the solvent, and the resulting nanotube membrane 51 may be a seal over polymer coating 50 with well-defined channels from polymer coating 50 to an outside. These well-defined channels may be of a uniform or nearly uniform diameter and may therefore provide a highly consistent flow rate of bioactive agent 14 from polymer coating 50 through nanotube membrane 51. If stent 12 is implanted in a human body, bioactive agent 14 may be released to the human body after flowing through nanotube membrane 51.

Figure 6:
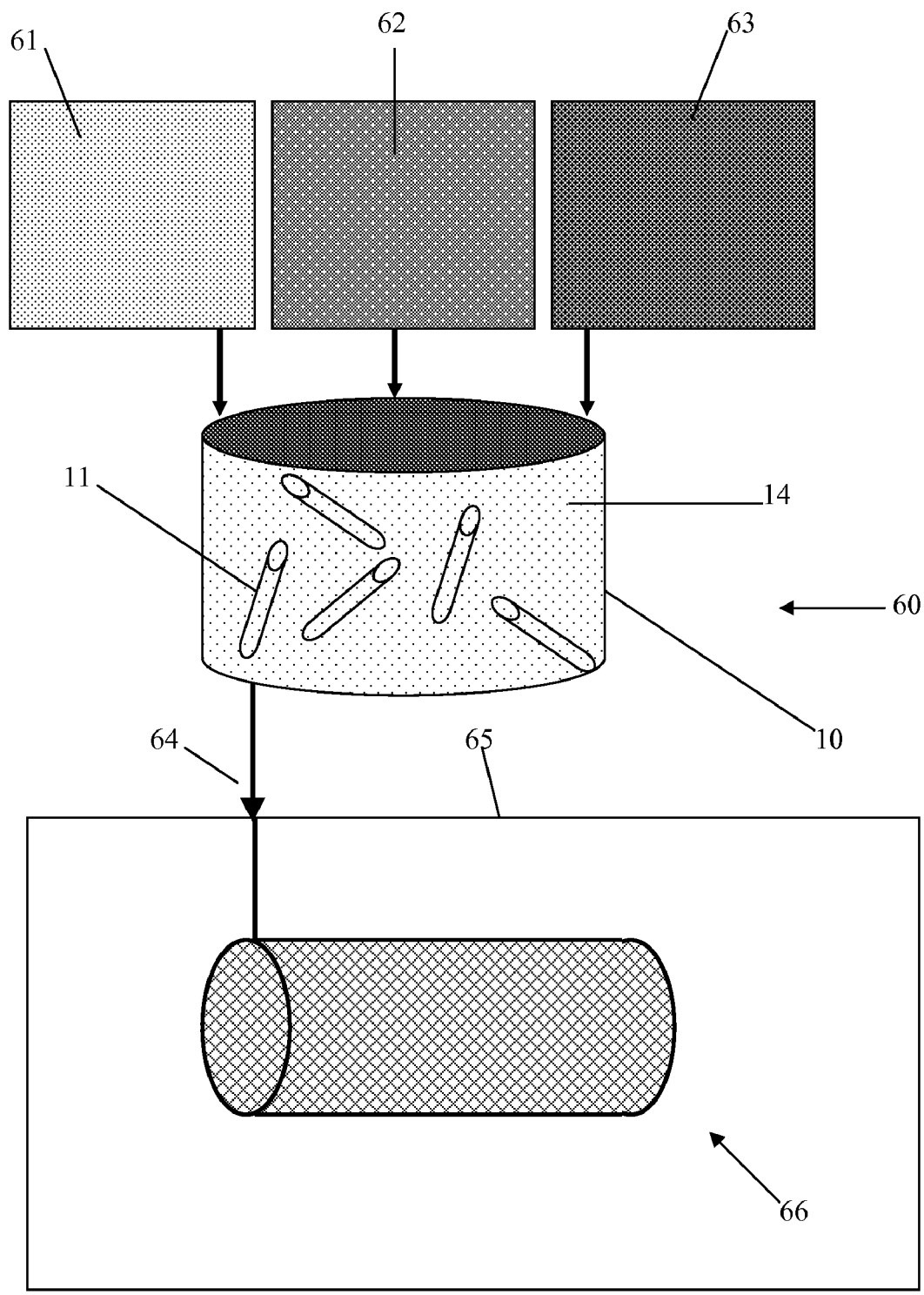
FIG. 6 shows a system for making a stent including nanotubes in the structure using an injection molding process.

FIG. 6 shows system 60 for making injection molded stent 66 including nanotubes 11 in the structure using an injection molding process. System 60 may include several source reservoirs for providing materials to system 60. System 60 of FIG. 6 is shown with three source reservoirs, namely therapeutic source 61, polymer source 62, and carbon nanotube precursor source 63. Each of sources 61, 62, 63 feed into mixing container 10. The contents of mixing container 10 therefore include bioactive agent 14, a polymer, and nanotubes 11. Mixing container 64 may have an active mixing arrangement, or may allow the materials from sources 61, 62, 63 to mix over time. Mixing container 64 may also be pressurized to promote flowing of the polymer combination. The contents of mixing container 64 may flow through valve 64 into mold 65, which may be an injection mold or an extrusion mold for a medical appliance. As shown in FIG. 6, mold 65 is for producing injection molded stent 66, and therefore allows the mixture flowing through valve 64 to fill, up a space in mold 65 that replicates the shape of stent 66. Mold 65 may maintain pressure on the mixture flowing through valve 64 until mold 65 is filled by the mixture. Thereafter, valve 64 may be closed and the pressure may be released from mold 65. After waiting an appropriate period for the mixture to solidify in the shape of injection molded stent 66, mold 65 may be opened and injection molded stent 66 may be removed.

Figure 7:
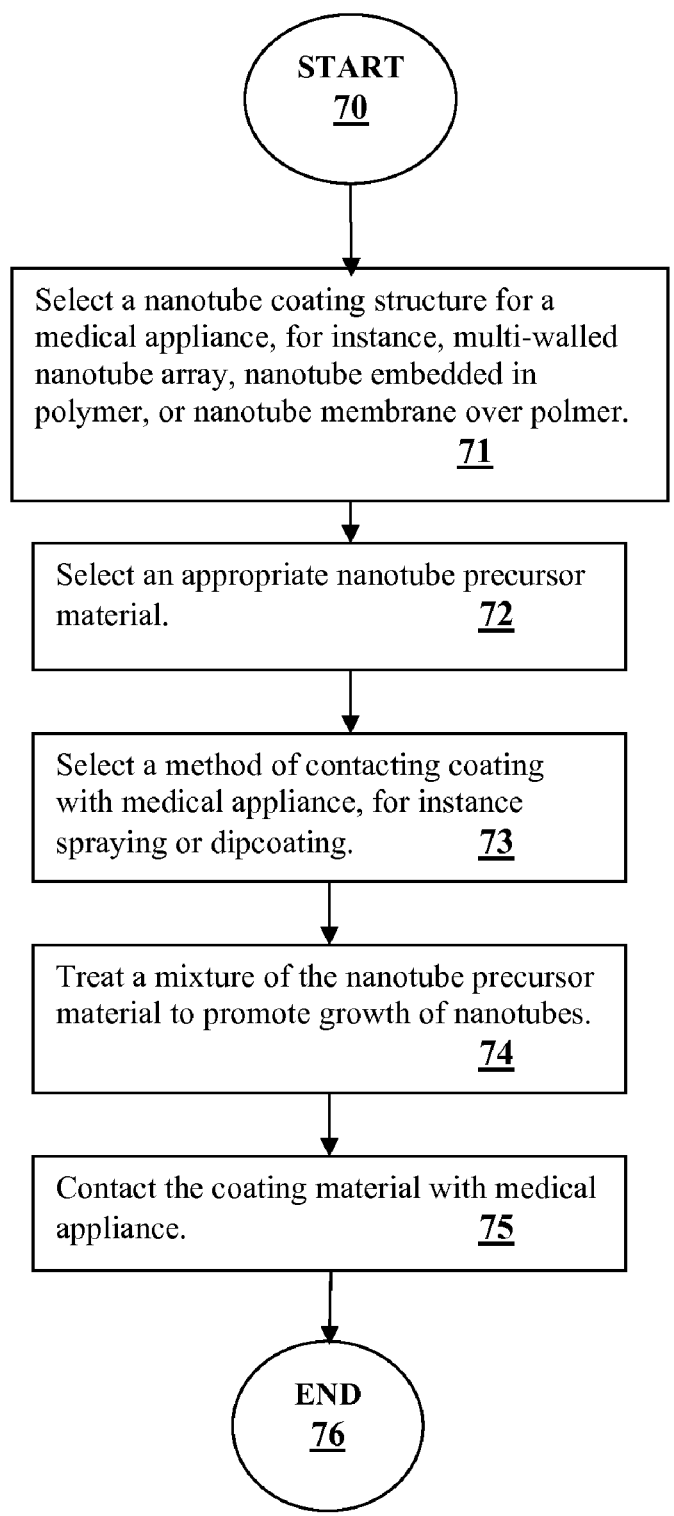
FIG. 7 is a flowchart for coating a medical appliance using nanotubes.

FIG. 7 is a flowchart for coating a medical appliance using nanotubes. The flow in FIG. 7 begins in start circle 70 and proceeds to action 71, which indicates to select a nanotube coating structure for a medical appliance, for instance, a multi-walled nanotube array, nanotubes embedded in a polymer, or a nanotube membrane over a polymer. From action 71 the flow proceeds to action 72, which indicates to select an appropriate nanotube precursor material. From action 72 the flow proceeds to action 73, which indicates to select a method of contacting coating with medical appliance, for instance spraying or dipcoating. From action 73 the flow proceeds to action 74, which indicates to treat a mixture of the nanotube precursor material to promote growth of nanotubes. From action 74 the flow proceeds to action 75, which indicates to contact the coating material with a medical appliance. From action 75 the flow proceeds to end circle 76.

As used herein, the term "bioactive agent" or "therapeutic agent" includes one or more "therapeutic agents" or "drugs". The terms "therapeutic agents", "active substance" and "drugs" are used interchangeably herein and include pharmaceutically active compounds, nucleic acids with and without carrier vectors such as lipids, compacting agents (such as histones), virus (such as adenovirus, andenoassociated virus, retrovirus, lentivirus and α-virus), polymers, hyaluronic acid, proteins, cells and the like, with or without targeting sequences.

The therapeutic agent may be any pharmaceutically acceptable agent such as a non-genetic therapeutic agent, a biomolecule, a small molecule, or cells.

Exemplary non-genetic therapeutic agents include anti-thrombogenic agents such heparin, heparin derivatives, prostaglandin (including micellar prostaglandin El), urokinase, and PPack (dextrophenylalanine proline arginine chloromethylketone); anti-proliferative agents such as enoxaprin, angiopeptin, sirolimus (rapamycin), tacrolimus, everolimus, monoclonal antibodies capable of blocking smooth muscle cell proliferation, hirudin, and acetylsalicylic acid; anti-inflammatory agents such as dexamethasone, rosiglitazone, prednisolone, corticosterone, budesonide, estrogen, estradiol, sulfasalazine, acetylsalicylic acid, mycophenolic acid, and mesalamine; anti-neoplastic/anti-proliferative/anti-mitotic agents such as paclitaxel, epothilone, cladribine, 5-fluorouracil, methotrexate, doxorubicin, daunorubicin, cyclosporine, cisplatin, vinblastine, vincristine, epothilones, endostatin, trapidil, halofuginone, and angiostatin; anti-cancer agents such as antisense inhibitors of c-myc oncogene; anti-microbial agents such as triclosan, cephalosporins, aminoglycosides, nitrofurantoin, silver ions, compounds, or salts; biofilm synthesis inhibitors such as non-steroidal anti-inflammatory agents and chelating agents such as ethylenediaminetetraacetic acid, O,O'-bis(2-aminoethyl)ethylenegly-col-N,N,N',N'-tetraacetic acid and mixtures thereof; antibiotics such as gentamycin, rifampin, minocyclin, and ciprofolxacin; antibodies including chimeric antibodies and antibody fragments; anesthetic agents such as lidocaine, bupivacaine, and ropivacaine; nitric oxide; nitric oxide (NO) donors such as lisidomine, molsidomine, L-arginine, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaprin, hirudin, warfarin sodium, Dicumarol, aspirin, prostaglandin inhibitors, platelet aggregation inhibitors such as cilostazol and tick antiplatelet factors; vascular cell growth promotors such as growth factors, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogeneus vascoactive mechanisms; inhibitors of heat shock proteins such as geldanamycin; and any combinations and prodrugs of the above.

Exemplary biomolecules include peptides, polypeptides and proteins; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Nucleic acids may be incorporated into delivery systems such as, for example, vectors (including viral vectors), plasmids or liposomes.

Non-limiting examples of proteins include monocyte chemoattractant proteins ("MCP-1) and bone morphogenic proteins ("BMP's"), such as, for example, BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15.Preferred BMPS are any of BMP-2, BMP-3, BMP-4, BMP-5, BMP-6, and BMP-7.These BMPs can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them. Non-limiting examples of genes include survival genes that protect against cell death, such as anti-apoptotic Bcl-2 family factors and Akt kinase and combinations thereof. Non-limiting examples of angiogenic factors include acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor, and insulin like growth factor. A non-limiting example of a cell cycle inhibitor is a cathespin D (CD) inhibitor. Non-limiting examples of anti-restenosis agents include p15, p16, p18, p19, p21, p27, p53, p57, Rb, nFkB and E2F decoys, thymidine kinase ("TK") and combinations thereof and other agents useful for interfering with cell proliferation.

Exemplary small molecules include hormones, nucleotides, amino acids, sugars, and lipids and compounds have a molecular weight of less than 100 kD.

Exemplary cells include stem cells, progenitor cells, endothelial cells, adult cardiomyocytes, and smooth muscle cells. Cells can be of human origin (autologous or allogenic) or from an animal source (xenogenic), or genetically engineered. Non-limiting examples of cells include side population (SP) cells, lineage negative (Lin−) cells including Lin−CD34−, Lin−CD34+, Lin−cKit+, mesenchymal stem cells including mesenchymal stem cells with 5-aza, cord blood cells, cardiac or other tissue derived stem cells, whole bone marrow, bone marrow mononuclear cells, endothelial progenitor cells, skeletal myoblasts or satellite cells, muscle derived cells, go cells, endothelial cells, adult cardiomyocytes, fibroblasts, smooth muscle cells, adult cardiac fibroblasts+5-aza, genetically modified cells, tissue engineered grafts, MyoD scar fibroblasts, pacing cells, embryonic stem cell clones, embryonic stem cells, fetal or neonatal cells, immunologically masked cells, and teratoma derived cells.

Any of the therapeutic agents may be combined to the extent such combination is biologically compatible.

Any of the above mentioned therapeutic agents may be incorporated into a polymeric coating on the medical device or applied onto a polymeric coating on a medical device. The polymers of the polymeric coatings may be biodegradable or non-biodegradable. Non-limiting examples of suitable non-biodegradable polymers include polystrene; polyisobutylene copolymers and styrene-isobutylene-styrene block copolymers such as styrene-isobutylene-styrene tert-block copolymers (SIBS); polyvinylpyrrolidone including cross-linked polyvinylpyrrolidone; polyvinyl alcohols, copolymers of vinyl monomers such as EVA; polyvinyl ethers; polyvinyl aromatics; polyethylene oxides; polyesters including polyethylene terephthalate; polyamides; polyacrylamides; polyethers including polyether sulfone; polyalkylenes including polypropylene, polyethylene and high molecular weight polyethylene; polyurethanes; polycarbonates, silicones; siloxane polymers; cellulosic polymers such as cellulose acetate; polymer dispersions such as polyurethane dispersions (BAYHDROL®); squalene emulsions; and mixtures and copolymers of any of the foregoing.

Non-limiting examples of suitable biodegradable polymers include polycarboxylic acid, polyanhydrides including maleic anhydride polymers; polyorthoesters; poly-amino acids; polyethylene oxide; polyphosphazenes; polylactic acid, polyglycolic acid and copolymers and mixtures thereof such as poly(L-lactic acid) (PLLA), poly(D,L,-lactide), poly(lactic acid-co-glycolic acid), 50/50 (DL-lactide-co-glycolide); polydioxanone; polypropylene fumarate; polydepsipeptides; polycaprolactone and co-polymers and mixtures thereof such as poly(D,L-lactide-co-caprolactone) and polycaprolactone co-butylacrylate; polyhydroxybutyrate valerate and blends; polycarbonates such as tyrosine-derived polycarbonates and arylates, polyiminocarbonates, and polydimethyltrimethylcarbonates; cyanoacrylate; calcium phosphates; polyglycosaminoglycans; macromolecules such as polysaccharides (including hyaluronic acid; cellulose, and hydroxypropylmethyl cellulose; gelatin; starches; dextrans; alginates and derivatives thereof), proteins and polypeptides; and mixtures and copolymers of any of the foregoing. The biodegradable polymer may also be a surface erodable polymer such as polyhydroxybutyrate and its copolymers, polycaprolactone, polyanhydrides (both crystalline and amorphous), maleic anhydride copolymers, and zinc-calcium phosphate.

Such coatings used with the present invention may be formed by any method known to one in the art. For example, an initial polymer/solvent mixture can be formed and then the therapeutic agent added to the polymer/solvent mixture. Alternatively, the polymer, solvent, and therapeutic agent can be added simultaneously to form the mixture. The polymer/solvent mixture may be a dispersion, suspension or a solution. The therapeutic agent may also be mixed with the polymer in the absence of a solvent. The therapeutic agent may be dissolved in the polymer/solvent mixture or in the polymer to be in a true solution with the mixture or polymer, dispersed into fine or micronized particles in the mixture or polymer, suspended in the mixture or polymer based on its solubility profile, or combined with micelle-forming compounds such as surfactants or adsorbed onto small carrier particles to create a suspension in the mixture or polymer. The coating may comprise multiple polymers and/or multiple therapeutic agents.

The coating can be applied to the medical device by any known method in the art including dipping, spraying, rolling, brushing, electrostatic plating or spinning, vapor deposition, air spraying including atomized spray coating, and spray coating using an ultrasonic nozzle.

The coating is typically from about 1 to about 50 microns thick. In the case of balloon catheters, the thickness is preferably from about 1 to about 10 microns, and more preferably from about 2 to about 5 microns. Very thin polymer coatings, such as about 0.2-0.3 microns and much thicker coatings, such as more than 10 microns, are also possible. It is also within the scope of the present invention to apply multiple layers of polymer coatings onto the medical device. Such multiple layers may contain the same or different therapeutic agents and/or the same or different polymers. Methods of choosing the type, thickness and other properties of the polymer and/or therapeutic agent to create different release kinetics are well known to one in the art.

The medical device may also contain a radio-opacifying agent within its structure to facilitate viewing the medical device during insertion and at any point while the device is implanted. Non-limiting examples of radio-opacifying agents are bismuth subcarbonate, bismuth oxychloride, bismuth trioxide, barium sulfate, tungsten, and mixtures thereof.

Non-limiting examples of medical devices according to the present invention include catheters, guide wires, balloons, filters (e.g., vena cava filters), stents, stent grafts, vascular grafts, intraluminal paving systems, implants and other devices used in connection with drug-loaded polymer coatings. Such medical devices may be implanted or otherwise utilized in body lumina and organs such as the coronary vasculature, esophagus, trachea, colon, biliary tract, urinary tract, prostate, brain, lung, liver, heart, skeletal muscle, kidney, bladder, intestines, stomach, pancreas, ovary, cartilage, eye, bone, and the like.

While the present invention has been described in connection with the foregoing representative embodiment, it should be readily apparent to those of ordinary skill in the art that the representative embodiment is exemplary in nature and is not to be construed as limiting the scope of protection for the invention as set forth in the appended claims.

What is claimed is:

1. A method of coating a medical device, comprising
   assembling an array of vertically-oriented carbon nanotubes on a surface of the medical device;
   contacting the array of carbon nanotubes with a liquid; and
   evaporating the liquid to form a cellular foam made of carbon nanotubes.

2. The method of claim 1, wherein a surface of the medical device is patterned, and wherein the array of carbon nanotubes is formed on the patterned surface.

3. The method of claim 1, wherein the liquid contains a polymer.

4. The method of claim 1, wherein the liquid is an organic solvent.

5. The method of claim 1, wherein the carbon nanotubes are multi-walled carbon nanotubes.

6. The method of claim 1, wherein the liquid contains a bioactive agent.

7. The method of claim 1, wherein the medical device is a balloon on a balloon catheter.

8. The method of claim 1, wherein the medical device is a stent.

9. A medical device having a coating made by the method of claim 1.

10. The medical device of claim 9, wherein the carbon nanotubes are multi-walled carbon nanotubes.

11. The medical device of claim 9, wherein the coating further comprises a polymer.

12. The medical device of claim 9, wherein the medical device is a balloon on a balloon catheter.

13. The medical device of claim 9, wherein the medical device is a stent.

* * * * *